Figure 1:
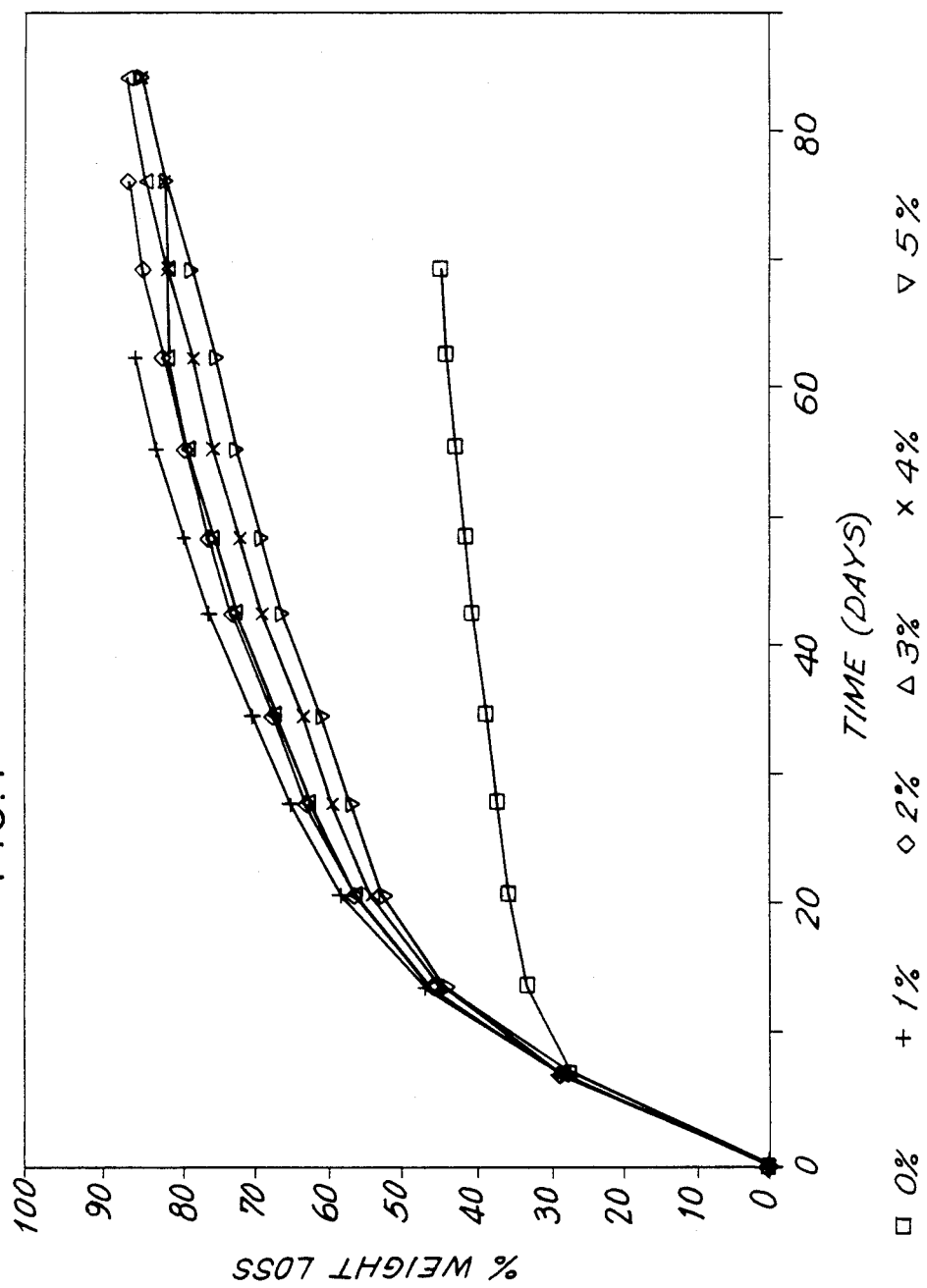

United States Patent [19]

Cashman et al.

[11] Patent Number: 4,983,578

[45] Date of Patent: Jan. 8, 1991

[54] AIR FRESHENER COMPOSITION AND DEVICE

[75] Inventors: Donald Cashman; John A. Ferguson; George B. Keyes, all of Cincinnati, Ohio

[73] Assignee: The Drackett Company, Cincinnati, Ohio

[21] Appl. No.: 339,345

[22] Filed: Apr. 18, 1989

[51] Int. Cl.$^5$ ............................................. A61K 7/46
[52] U.S. Cl. ..................................... 512/3; 424/76.1; 424/76.2; 239/44
[58] Field of Search .................. 512/3; 424/76.1, 76.2; 239/44

[56] References Cited

U.S. PATENT DOCUMENTS 4,078,055  3/1978  Naganuma et al. ................ 424/76.2
4,663,081  5/1987  Grimshaw et al. ..................... 512/3

*Primary Examiner*—James H. Reamer
*Attorney, Agent, or Firm*—Sandra M. Nolan

[57] ABSTRACT

A novel air freshener composition and a combination product which uses same in an a device which has an emanator are described. The composition employs a combination of reagents which inhibit its evaporation so that the useful life of the air freshener is significantly lengthened.

13 Claims, 3 Drawing Sheets

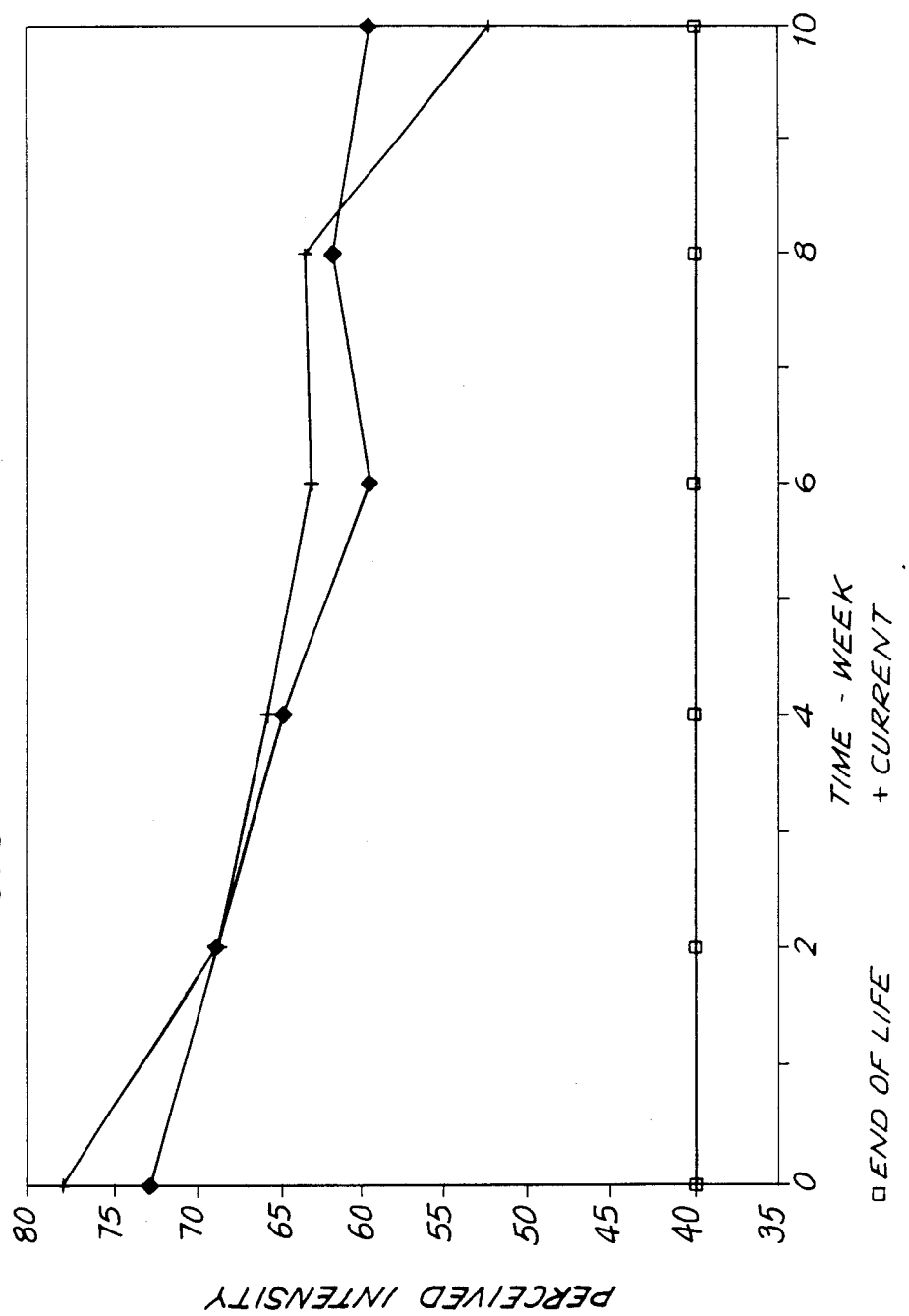

AIR FRESHENER COMPOSITION AND DEVICE

BACKGROUND

Air fresheners typically are dispensed into the air from devices which have, in combination, a rigid wick, or other transfer means, which contacts, on one end or portion thereof, a reservoir of liquid air freshener and on the other end, or a different portion of the wick, an emanator or diffusion means, which emanator is more porous than the wick means and does not contact the reservoir. It has been found that the porosity of the emanator or other diffusion means has a direct bearing on the effectiveness of the air freshener composition in terms of such factors as duration of use of a fixed quantity of air freshener composition (i.e., evaporation rate) and intensity of vapors emanating from the device (i.e., fragrance intensity).

Known devices of the type contemplated for use with the compositions of the invention are disclosed in U.S Pat. Nos. 4,413,779 and 4,739,928.

U.S. No. 4,413,779 to Santini deals with a vaporizing device for an air freshener composition which device is composed of a rigid nylon wick which contacts a reservoir on one end and a hemispheric diffuser surface which is highly porous on the other.

U.S. No. 4,739,928 which is assigned to Applicant's assignee, deals with an air freshener dispenser which has a wick which contacts both a container of air freshener liquid and a porous emanator pad.

A composition designed for use in a reservoir/wick-/emanator device such as that with which Applicant's compositions can be used is described in U.S. No. 4,663,081 (and E.P.O. Publn. No. 194017A1, Appln. 86300604.5) to Grimshaw et al (inventors). That patent describes the same general type of device from which Applicant's composition can be dispensed as well. The compositions disclosed in this patent contain water, diethylene glycol monobutyl ether, and perfume. The glycol ether's volatility assists in the migration of the evaporated air freshener through the wick or other transfer means and to the emanator pad.

As the Grimshaw et al patent points out, the volatility of the volatile component(s) of such a composition must be such that the total composition—including the perfume—reaches the emanator for dissipation into the air. If the volatility of such component(s) is too great, they will evaporate too quickly, leaving the perfume in the reservoir.

Less preferred devices from which the compositions of the invention can be dispensed into the atmosphere are wafer- or pad-like devices U.S. No. 4,367,203 shows such a device. The composition passes through holes or tunnels in the outer or emanator surface(s) of such a device via wick-like action.

Unless otherwise indicated, the disclosures of all of the publications mentioned herein are hereby incorporated by reference.

THE INVENTION

It has been discovered that, in an air freshener which is useful in a device which has an emanator surface and, preferably, employs an emanator/wick/reservoir system, maximum air freshening efficiency is attainable over a longer period of time by proper manipulation of the composition and the ingredients of the formulations. It has been found that compositions in which the ratio of low volatile solvent to non-volatile emulsifier is from about 1:0.13 to about 1:75 are highly effective. These compositions are particularly useful in systems where about 50% of the pore volume in the emanator and/or emanator surface became clogged too early in their expected use life, by non-volatiles of the liquid.

In a preferred embodiment, a glycol ether, preferably diethylene glycol monoethyl ether, interacts with the emulsifier(s) in the pore spaces in the emanator to extend the useful life of the product up to 240%. The preferred compositions contain about 0.1% to about 15 wt% of a glycol ether of the requisite volatility, along with about 2 to 15 wt% of an emulsifier, about 3 to 20 wt% of an alcohol and q.s to 100 wt% of one or more other component(s) selected from perfumes, co-solvents, neutralizers pigments and water. In highly preferred embodiments, the ratio of low volatile solvent to non-volatile emulsifier is from about 1:1 to about 1:7.5 when used in emanator systems that previously evaporated too quickly and thereby experienced a shorter than desired product use life. It is believed that as the total composition flows through the wick and into the emanator the glycol ether preferentially occupies the port volume of the emanator such that when the combined volume of glycol ether and emulsifier approach about 50% or lower, pore volume, a more controlled rate of evaporation is attained.

ADVANTAGES

The compositions of the invention have several advantages over other wick type air freshener formulations. They are sufficiently volatile that the surrounding air into which they emanate is noticeably fragranced However, they are not so volatile that their useful emanating lives are too short for an intended long lasting continuous acting air freshener. In fact, when the proper combination of the glycol ether of this invention and the hydroxyphosphoric acid component is used, the dispensing length of life of the product (i.e., the combination of composition and device) is increased from a normal 25 days to up to 60 days a 240% increase. In other words, the composition is dispensed to, and fragrance emanates from, the emanator surface of the device for a period of time which is up to 2.4 times that which a conventional air freshener, without the glycol ether, would function.

In addition, the compositions of the invention help prevent the clogging of the pores and/or conduits of the dispenser. This ability to retard clogging assist in enhancing the useful life of the product.

DESCRIPTION OF THE INVENTION

These and other features of the invention will be apparent after a consideration of the following description of the invention.

The invention is concerned with air freshener compositions which are formulated to be used with particular types of emanators, emanator/wick, and emanator/-wick/reservoir systems. These systems are embodied in a variety of devices from which the compositions can be dispensed into the atmosphere under ambient, i.e. normal, temperature and pressure conditions.

DEVICES

Useful devices include those described above under "Background". In addition, the compositions of the invention can be dispensed for such devices as described in U.S Pat. Nos. 3,679,133; 4,323,191; and the like.

The key features of the emanator systems with which the composition are used are reservoir, wick or transfer conduit and emanator surface.

COMPOSITIONS

The compositions of the invention contain three essential components. They are:

(a) a hydroxyphosphoric acid, which functions to couple and emulsify, (b) a glycol ether which serves to control and prolong evaporization, and (c) an alcohol solvent, which serves to solubilize and couple.

THE HYDROXYPHOSPHORIC ACID

The hydroxyphosphoric acid ingredient is one of a group of compounds of the general formula $$R(OCH_2CH_2)_xOPO_3H_2$$

wherein R is an alkylphenol moiety, preferably nonylphenol, and x is an integer between about 3 and about 15, preferably about 8 to about 11.

One highly preferred material is Monafax 785 ™ a product of Mona Industries, Inc of Paterson, N.J.), the exact formula of which is proprietary. It is believed to be a acid, typically referred to as a phosphate ester emulsifier (see McCutcheon's Emulsifiers and Detergents, North American Edition 1985, page 212).

Monafax 786 ™ (from Mona Industries) is also highly preferred. It is nonoxynol-6 phosphate and is described at page 55 of the CTFA Cosmetic Ingredient Dictionary, J.M. Whelan, ed. 3rd ed. Supp. (1985).

Another commercial phosphate ester emulsifier suitable for use in this invention is available as Phosphorester 610 from the Sandoz Chemicals Corporation of Charlotte, N.C. (In Sandoz bulletin #7-477/83, it is described as having exceptional solubility and as being an excellent emulsifier, even in high concentrations of alkali and salts. The manufacturer described it as a solubilizer of nonionic surfactants and as an emulsifier for aromatic and chlorinated solvents.)

One additive conveniently employed along with the phosphoric acid reagent is a neutralizer. Alkaline agents, such as alkali metal and alkaline earth metal oxides and hydroxides, are useful in suitable quantities.

Other useful neutralizer materials of this type include ammonia, and the lure. Mixtures are operable.

POLYALKYLENE GLYCOL ALKYL ETHER

The second required component is a polyalkylene glycol alkyl ether. Dialkyline glycol monoalkyl ethers are preferred. Diethylene glycol monoethyl ether is highly preferred.

One particularly useful material of this type is the ethoxy-diglycol product sold as Dowanol DE ™ by Dow Chemical (Midland, Michigan or Carbitol, Low Gravity ™, as sold by Union Carbide Corp. of Danbury, CT. The compound can also be called 2-(2-ethoxyethoxy) ethanol.

This component of the composition functions as an evaporation inhibitor, especially under certain conditions to be discussed hereinbelow.

ALCOHOL

The alcohol solvents used in the compositions of the invention are essential not only because they help to solubilize and couple the highly hydrophobic components of the fragrance oils into a basically aqueous system, but also because that they do so without becoming a predoment note in the overall character of the fragrance.

Generally, useful alcohols are monoalcohols containing from about 2 to about 12, preferably about 2 to about 6, carbon atoms. The carbon chains may be straight, branched or cyclic. When 3 or more carbon atoms are present, branched chain alcohols are preferred.

One highly preferred group are alcohols including isopropyl alcohol, propyl alcohol, ethyl alcohol and the like. Mixtures are operable.

EXCIPIENTS

The air freshener compositions of the invention may contain a wide variety of excipients. In addition to water and other cosolvents or diluents, they may also contain at least one other conventional additive, such as one or more perfumes, colorants, neutralizers, stabilizers, and the like.

AMOUNTS OF INGREDIENT

The following table gives approximate weight percentage ranges for the ingredients used in the compositions of the invention. A skilled artisan can extrapolate from the values given in order to tailor a composition to his specific needs.

Unless otherwise stated, all percentages recited in the specification are weight percentages based on total composition weight.

|  | Broad | Preferred | Highly Preferred |
|---|---|---|---|
| Phosphoric Acid | 2.0–15.0 | 4.0–10.0 | 5.0–8.0 |
| Neutralizer for acid* | 0.01–2.0 | 0.2–1.5 | 0.3–1.0 |
| Alkylene glycol ether | 0.1–15.0 | 0.1–10.0 | 0.5–5.0 |
| Alcohol(s) | 3.0–20.0 | 4.0–15.0 | 4.0–10.0 |
| Perfume | 2.0–12.0 | 3.0–8.0 | 3.0–6.0 |
| Colorant | 0.00001–.005 | 0.00001–.003 | 0.00001–.002 |
| Other excipient(s) | 0–20.0 | 0–15 | 0–10 |
| Water | q.s. to 100 | q.s. to 100 | q.s. to 100 |

*In the following examples, a 50% active aqueous solution of sodium hydroxide was employed as a neutralizer.

The interaction between the ingredients of the composition is not totally understood. However, Applicants have found that the effective in-use length of life of air fresheners using this composition can be significantly lengthened without a significant drop in perceived fragrance intensity when the ratio of the low volatile solvent to the non-volatile phosphate ester emulsifier ranges from about 1:0.13 to about 1:75. Without the addition of the low volatile solvent to the composition the in-use length of life of the dispensing air freshening device is noticeably shorter.

One explanation for this observation of slower, more controlled, release rate of the composition from appropriate devices seems to center on the accessibility of the pore volume (or porosity) of the emanator. That is, it has been found that when the emanator pore volume decreases to approximately one-half its original value, the evaporization rate of the composition and, therefore, the intensity of vaporized fragrance decrease significantly.

In compositions not containing the water miscible, low volatile solvent of this invention, the decrease in emanator pore volume is caused by the build up of the non-volatile emulsifier in the emanator. As the emulsifier concentrates in the emanator, the flow of the composition to the emanator surface, where the volatiles vaporize into the surrounding air, is hampered and reduced. Above and beyond the emulisifier's mere physical presence to reduce flow of the composition, the flow is also restricted by the fact that as the phosphate ester emulsifier concentrates in the emanator pad, it increases in viscosity. All of this does not occur, however, until after a large portion of the product has evaporated. That is, the evaporization rate does not begin to decrease until the volume of liquid in the emanator is approximately 50% saturated with the non-volatile emulsifier.

Surprisingly, the compositions of this invention using the low volatile water miscible solvent and the phosphate ester emulsifier slow down evaporization employing a very different mechanism. It appears that the low volatile solvent, e.g., diethylene glycol monoethyl ether, competes with the emulsifier for some of the emanator pore volume, temporarily occupying some of the pores of the emanator pad and surface and, thereby, denying normal flow and evaporization of the fragrance oil from the pad surface. The low volatile solvent, unlike the emulsifier, does not concentrate or remain in the pad; it does not increase in viscosity in the pad. In fact, it combines with the non-volatile emulsifier that is present to provide an efficient controlled flow and release of the volatiles over time without negatively impacting on perceived product performance, relative to fragrance intensity.

While not wishing to be bound by any theory, Applicants note that the useful life of their compositions, when used with the types of emanators, emanator/wick and emanator/wick/reservoir devices contemplated, is about 25 to 60 days. That is, about 2.4 times the length-of-life of conventional air freshener composition/device combinations.

The extension of useful life appears to depend on the ratio of ether to emulsifier, such that ether:emulsifier ratios of about 1:1 to about 1:7.5 are preferred.

The amount of the air freshener composition used in the products of the invention is not critical. It is a function of such variables as the size of the reservoir, the area of the emanator surface, etc.

EXAMPLES

The following examples illustrate the preparation and use of the compositions and composition/device combination of the invention.

In the examples, the following steps were followed to mix the ingredients:

1. Add the alcohol(s) to a minor amount (generally about 8%) of the water and mix well.
2. Add fragrance(s) and mix well.
3. Add sodium hydroxide or other neutralizer and mix well.
4.* Add the glycol ether and mix well.
5. Add the remainder of the water (generally q.a. 100%) and mix well.
6.* Add colorant/pigment and mix.

*Steps 4 and 6 may be omitted, depending upon the final formulation desired.

It should be noted that other conventional methods of preparation can be used to prepare the formulations of the invention.

EXAMPLE I

The inclusion of diethylene glycol monoethyl ether not only provides the composition/device combinations of this invention with a longer use life (improved control over product delivery length-of-life), but also prevents the clogging of the wick and/or emanator system when employed with certain fragrances typically found in conventional wick type air fresheners.

A typical formulation wherein this clogging occurred was:

| Material | % By Weight |
| --- | --- |
| Noville Fragrance #30588 | 4.0 |
| Monafax 785 | 6.0 |
| Isopropyl alcohol | 8.0 |
| 50% Sodium Hydroxide | 0.7 |
| Deionized Water | q.s. to 100 |
| | 100.0 |

Using the above composition, clogging of the system was visible after only two weeks activation (samples run in duplicate) while similar compositions containing the low-volatile solvent at increasing levels continued to deliver the compositions to the emanator and the devices fragranced the surrounding air over their extended use life. Monitoring the weight loss data for those samples that did not clog was discontinued after the percent weight loss approximated 85%. See Table I and FIG. 1.

TABLE I

| | AVERAGE % WEIGHT LOSS | | | | | | | | | | | | |
| --- | --- | --- | --- | --- | --- | --- | --- | --- | --- | --- | --- | --- | --- |
| | TIME (DAYS) | | | | | | | | | | | | |
| | 0 | 7 | 14 | 21 | 28 | 35 | 43 | 49 | 56 | 63 | 70 | 77 | 85 |
| NO DE | 0 | 27.42 | 33.62 | 35.77 | 37.38 | 38.92 | 40.77 | 41.69 | 42.92 | 44.00 | 45.38 | — | — |
| 1% DE | 0 | 28.44 | 47.08 | 58.31 | 65.15 | 70.37 | 76.46 | 79.62 | 83.31 | 85.92 | — | — | — |
| 2% DE | 0 | 25.18 | 46.15 | 56.77 | 63.08 | 67.34 | 73.15 | 76.00 | 79.23 | 81.92 | 84.77 | 86.46 | — |
| 3% DE | 0 | 29.21 | 46.23 | 56.38 | 62.15 | 66.78 | 72.46 | 75.38 | 78.77 | 81.54 | 81.23 | 84.15 | 86.77 |
| 4% DE | 0 | 28.91 | 45.08 | 54.38 | 59.54 | 63.65 | 69.31 | 72.00 | 75.54 | 78.31 | 81.54 | 82.31 | 85.23 |
| 5% DE | 0 | 29.47 | 44.23 | 52.62 | 57.38 | 60.99 | 66.46 | 69.15 | 72.46 | 75.08 | 78.38 | 81.85 | 84.69 |

DE = Dowanol DE

EXAMPLE II

In another experiment testing the application of the low-volatile solvent, diethylene glycol monoethyl ether, compositions of the invention using six completely different fragrances were formulated and tested, in triplicate, for weight loss due to product emanation over their useful life.

The data was averaged for all samples every two weeks up to 10 weeks and compared to control samples without the solvent. See Table II and FIG. 2.

TABLE II

| | PERCENT WEIGHT LOSS | | | | |
| --- | --- | --- | --- | --- | --- |
| | TIME (WEEKS) | | | | |
| PRODUCT | 2 | 4 | 6 | 8 | 10 |
| Control (without low volatile solvent) | 35.7 | 53.7 | 76.8 | 83.5 | 85.8 |
| Variable (with low volatile solvent) | 33.0 | 52.4 | 66.6 | 74.1 | 78.9 |

Figure 2:
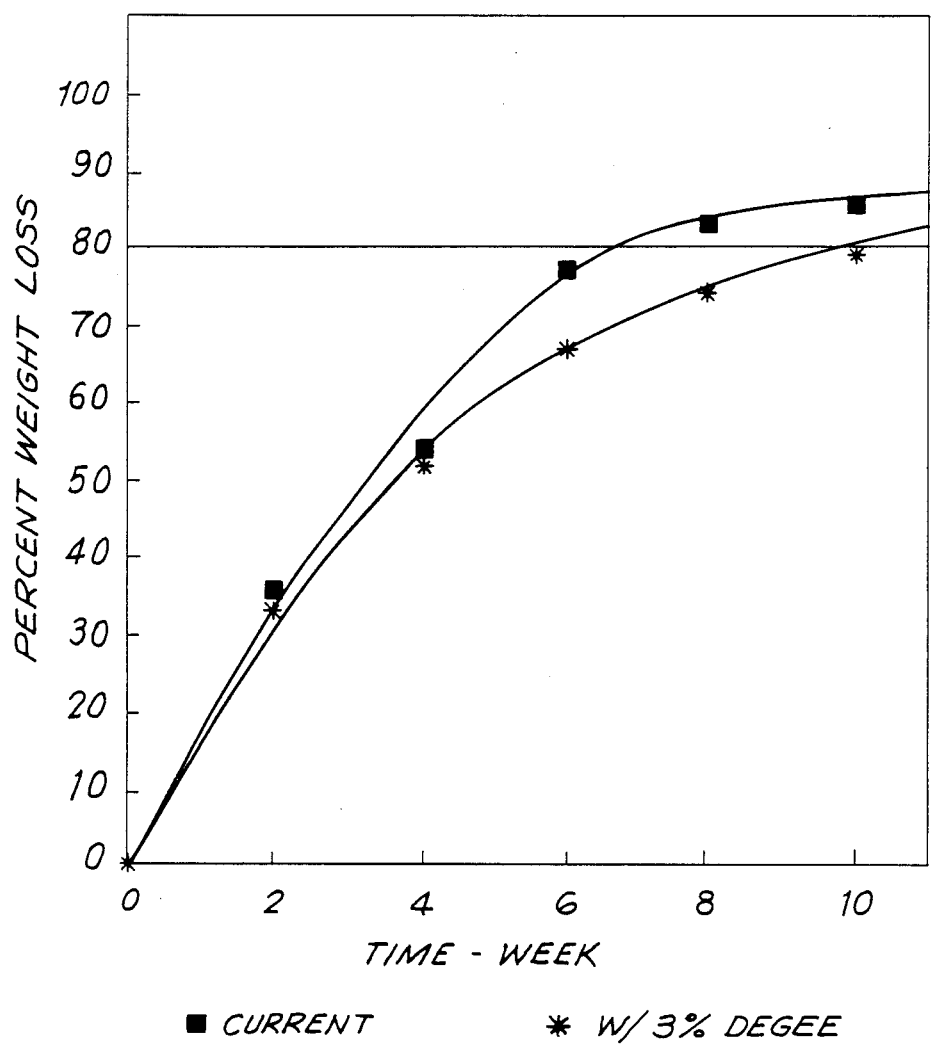

As can be seen in FIG. 2, the length of life of the averaged data of the diethylene glycol monoethyl ether formulas was increased by at least 26%. This is determined by the point where liquid was no longer visible in the units and the weight loss had reached 80%.

The fragrance intensity of the two series of formulas was also evaluated during the 10 weeks testing The results show that the low-volatile solvent containing formulas were judged by panelists to be essentially the same. See FIG. 3 and Table III.

TABLE III

| (0-160 MAGNITUDE ESTIMATION SCALE) | | | | | | |
| --- | --- | --- | --- | --- | --- | --- |
| | FRAGRANCE INTENSITY OVER TIME (WEEKS) | | | | | |
| PRODUCT | 0 | 2 | 4 | 6 | 8 | 10 |
| Control formulas (no low volatile solvent) | 78 | 69 | 66 | 63 | 64 | 52 |
| Variable formulas (with 3% low volatile solvent) | 73 | 69 | 65 | 60 | 62 | 60 |

No particular type of mixer need be used to prepare the compositions of the invention. Any system—including hand mixing—which assures sufficient agitation of the ingredients is suitable A conventional propeller mixer is typically employed.

Reasonable variations, such as those which would occur to a skilled artisan, can be made herein without departing from the scope of the invention.

We claim:

1. An air freshener composition consisting essentially of:
    (a) from about 2 to about 15 wt% of a phosphoric acid surfactant of the general formula $R(OCH_2CH_2)_xOPO_3H_2$ wherein R is a nonylphenol moiety and x is an integer between about 3 and about 15,
    (b) from about 0.1 to about 15 wt.% of diethylene glycol monoethylether,
    (c) from about 3 to about 20 wt.% of at least one $C_{2-12}$ alcohol solvent,
    (d) from about 2 to 12 wt.% perfume,
    (e) from about 0 to about 20 wt.% of other excipients, and
    (f) q.s. 100 wt.% water,
    wherein the ratio of the low volatile ingredient(s) to the non-volatile ingredient(s) is from about 1:0.13 to about 1:75.

2. The composition of claim 1 which contains from about 4 to about 10 wt% of (a), from about 0.1 to about 10% of (b), and from about 4 to about 15 wt% of (c).

3. The composition of claim 2 wherein (a) is the compound in which x in the formula has a value of about 8 to about 11.

4. An air freshener product comprising:
    (1) a container for an air freshener composition, comprising an emanating surface and a wick for supplying the solution to the emanating surface, and
    (2) an air freshener composition consisting essentially of the composition of claim 1.

5. The air freshener product of claim 4 wherein the ratio of the low volatile ingredient(s) to the non-volatile ingredient(s) is from about 1:1 to about 1:7.5.

6. In an air freshener composition for use in an air freshener device having a solid wick, which composition contains at least one perfume, at least one alcohol solvent, and at least one phosphoric acid surfactant, the improvement wherein from about 0.1 to about 10 wt.% of diethylene glycol monoethyl ether is employed as an evaporation inhibitor and the ratio of ether to surfactant is from about 1:1 to about 1:75.

7. The composition of claim 6 wherein the phosphoric acid surfactant is of the general formula $R(OCH_2CH_2)_xOPO_3H_2$ wherein R is an alkylphenol moiety and x an integer between about 3 and about 15.

8. The composition of claim containing from about 0.5 to about 5% of the evaporation inhibitor.

9. A process of inhibiting the evaporation of an air freshener composition from a device comprising an emanator, which process includes he step of incorporating into the composition an evaporation inhibiting amount of diethylene glycol monoethyl ether and an emulsifying amount of phosphoric acid surfactant of the formula $R(OCH_2CH_2)_xOPO_3H_2$ wherein R is a nonylphenol moiety and x an integer between about 3 and about 15.

10. The process of claim 9 wherein the ether is used in a concentration of from about 0.5 to about 5 wt% of the composition.

11. The composition of claim 1 wherein the alcohol solvent comprises a $C_{2-6}$ alcohol.

12. The composition of claim 11 wherein the alcohol solvent comprises at least one compound selected from the group consisting of isopropyl alcohol, propyl alcohol and ethyl alcohol.

13. The composition of claim 11 wherein the alcohol solvent comprises isopropyl alcohol.

* * * * *